(12) United States Patent
Winqvist et al.

(10) Patent No.: US 11,672,842 B2
(45) Date of Patent: Jun. 13, 2023

(54) GONADOTROPIN-RELEASING HORMONES FOR USE AS ADJUVANT IMMUNOTHERAPEUTICS

(71) Applicant: ISR IMMUNE SYSTEM REGULATION HOLDING AB (PUBL), Solna (SE)

(72) Inventors: Ola Winqvist, Uppsala (SE); Yen Lundgren, Västra Frölunda (SE)

(73) Assignee: ISR IMMUNE SYSTEM REGULATION HOLDING AB (PUBL), Stockholm (SE)

(*) Notice: Subject to any disclaimer, the term of this patent is extended or adjusted under 35 U.S.C. 154(b) by 764 days.

(21) Appl. No.: 16/487,772

(22) PCT Filed: Feb. 22, 2018

(86) PCT No.: PCT/EP2018/054347
§ 371 (c)(1),
(2) Date: Aug. 21, 2019

(87) PCT Pub. No.: WO2018/153961
PCT Pub. Date: Aug. 30, 2018

(65) Prior Publication Data
US 2021/0128672 A1 May 6, 2021

(30) Foreign Application Priority Data
Feb. 22, 2017 (EP) .................................. 17157388

(51) Int. Cl.
| | | |
|---|---|---|
| *A61K 31/05* | (2006.01) | |
| *A61K 31/565* | (2006.01) | |
| *A61K 31/566* | (2006.01) | |
| *A61K 31/568* | (2006.01) | |
| *A61K 31/5685* | (2006.01) | |
| *A61K 31/57* | (2006.01) | |
| *A61K 31/58* | (2006.01) | |
| *A61K 38/09* | (2006.01) | |
| *A61P 31/12* | (2006.01) | |
| *A61P 31/18* | (2006.01) | |
| *A61P 37/04* | (2006.01) | |
| *A61K 31/567* | (2006.01) | |

(52) U.S. Cl.
CPC .............. *A61K 38/09* (2013.01); *A61K 31/05* (2013.01); *A61K 31/565* (2013.01); *A61K 31/566* (2013.01); *A61K 31/567* (2013.01); *A61K 31/568* (2013.01); *A61K 31/5685* (2013.01); *A61K 31/57* (2013.01); *A61K 31/58* (2013.01); *A61P 31/18* (2018.01); *A61P 37/04* (2018.01)

(58) Field of Classification Search
CPC combination set(s) only.
See application file for complete search history.

(56) References Cited

U.S. PATENT DOCUMENTS

| | | |
|---|---|---|
| 7,834,141 B1 | 11/2010 | Siler-Khodr |
| 8,349,805 B2 | 1/2013 | Bevec et al. |
| 9,388,216 B2 | 7/2016 | Millar et al. |
| 2004/0152639 A1 | 8/2004 | Siler-Khodr |
| 2004/0235748 A1 | 11/2004 | Igari |
| 2004/0259803 A1 | 12/2004 | Boyd |
| 2005/0043245 A1 | 2/2005 | Siler-Khodr |
| 2011/0129532 A1* | 6/2011 | Ljungblad .............. A61K 45/06 514/3.7 |
| 2012/0045393 A1 | 2/2012 | Linder |

FOREIGN PATENT DOCUMENTS

| | | |
|---|---|---|
| EP | 1382350 A1 | 1/2004 |
| GB | 2237571 A | 5/1991 |
| JP | 2003-012552 A | 1/2003 |
| JP | 2004-512011 A | 4/2004 |
| JP | 2007-518699 A | 7/2007 |
| JP | 2009-539952 A | 11/2009 |
| JP | 2010-539008 A | 12/2010 |
| WO | 200174377 A1 | 10/2001 |
| WO | 200230435 A1 | 4/2002 |
| WO | 2003051272 A2 | 6/2003 |
| WO | WO 2004/094599 A2 | 11/2004 |
| WO | WO 2004/103271 A3 | 12/2004 |
| WO | 2007144554 A2 | 12/2007 |
| WO | 2009033663 A1 | 3/2009 |
| WO | WO 2009/033701 A1 | 3/2009 |
| WO | 2009145690 A1 | 12/2009 |
| WO | 2018134372 A1 | 7/2018 |

OTHER PUBLICATIONS

Overview of Viruses, Merck Manuals, accessed May 1, 2017 at URL merckmanuals.com/professional/infectious-diseases/viruses/overview-of-viruses, pp. 1-5 (Year: 2017).*
Illing et al., "Comparative Sequence Analysis and Functional Characterization of the Cloned Sheep Gonadotropin-releasing Hormone Receptor Reveal Differences in Primary Structure and Ligand Specificity among Mammalian Receptors," *Biochemical and Biophysical Research Communications*, 1993, 196(2), 745-51, 2 pages.
immunopaedia.org, "Internet archive of 4. MHC & Antigen Presentation," Dec. 8, 2016, Retrieved from internet on Nov. 18, 2021, https://web.archive.org/web/20161208044034/https://www.immunopaedia.org.za/immunology/basics/4-mhc-antigen-presentation/, 8 pages.
Iseda and Matano, "Progress toward prevention and cure of HIV infection" with abridged English translation, AIDS Research Center, National Institute of Infectious Diseases, vol. 33, No. 17, 2015, pp. 2727-2731.
Limonta et al., "GnRH receptors in cancer: From cell biology to novel targeted therapeutic strategies," *Endocrine Reviews*, Oct. 2012, 33(5):784-811).

(Continued)

*Primary Examiner* — Julie Ha
*Assistant Examiner* — Kristina M Hellman
(74) *Attorney, Agent, or Firm* — Glenn Foulds; Carl A. Morales; Fenwick & West LLP (57) ABSTRACT

The present invention relates to the use of a gonadotropin-releasing hormone (including GnRH I, a GnRH I analogue, GnRH II, or a GnRH II analogue) as adjuvant immunotherapeutic.

18 Claims, 8 Drawing Sheets

(56) References Cited

OTHER PUBLICATIONS

National Cancer Institute, "What is Cancer?" retrieved online on Sep. 24, 2021 from https://www.cancer.gov/about-cancer/understanding/what-is-cancer, 8 pages.

Kamaruzzaman, N. et al., "Targeting the hard to reach: challenges and novel strategies in the treatment of intracellular bacterial infections," *British Journal of Pharmacology*, vol. 174, Issue 14, 2016, pp. 2225-2236.

ITH/ISR Immune System Regulation: "An open phase II study in HIV-1 infected untreated male adult patients to evaluate safety and tolerability and the in vivo effects on T cell population and viral load of a GnRH analogue administered by intranasal administration during 28 days when combined with a single intramuscular testosterone depot injection to restore a normal serum testosterone level", Apr. 30, 2014 (Apr. 30, 2014), pp. 1-13, XP055394073.

Saussez et al., 2014 "Towards neuroimmunotherapy for cancer: the neurotransmitters glutamate, dopamine and GnRH-II augment substantially the ability of T cells of few head and neck cancer patients to perform spontaneous migration, chemotactic migration and migration towards the autologous tumor, and also elevate markedly the expression of CD3zeta and CD3epsilon TCR-associated chains," J Neural Transm (Vienna) 121(8):1007-27.

International Search Report of the International Searching Authority for Application No. PCT/EP2018/054347, dated May 14, 2018, 4 pages.

Written Opinion of the International Searching Authority for Application No. PCT/EP2018/054347, dated May 14, 2018, 7 pages.

International Preliminary Report on Patentability for PCT/EP2018/054347, dated May 16, 2019, 19 pages.

Doron, Bacterial infections: Overview; International Encyclopedia of Public Health, 2008:273-282.

Garcia-Gomez, Role of Sex Steroid Hormones in Bacterial-Host Interactions; Hindawi 2013 vol. 2013, Article ID 928290 (11 pages).

Millar et al., 1989 "Chimeric Analogues of Vertebrate Gonadotropin-releasing Hormones Comprising Substitutions of the Variant Amino Acids in Positions 5, 7, and 8. Characterization of requirements for receptor binding and gonadotropin release in mammalian and avian pituitary gonadotropes," J Biol Chem 264(35):21007-13.

CDC (https://www.cdc.gov/fungal/diseases/index.html accessed May 21, 2021) (2 pages).

National Institute of Health (https://www.niaid.nih.gov/research/antimicrobial-resistance-threats Feb. 11, 2020) (3 pages).

Illing, Biochemical and Biophysical Research Communications, 1993, 196(2), 745-51 (Year: 1993).

\* cited by examiner

GONADOTROPIN-RELEASING HORMONES FOR USE AS ADJUVANT IMMUNOTHERAPEUTICS

FIELD OF THE INVENTION

The present invention relates to the use of a gonadotropin-releasing hormone (including GnRH I, a GnRH I analogue, GnRH II, or a GnRH II analogue) as an adjuvant immunotherapeutic. The use of a GnRH and analogues thereof minimizes the risk of progression of a viral disease, notably HIV. The present invention also relates to pharmaceutical compositions or pharmaceutical kits comprising a gonadotropin-releasing hormone for use as adjuvant immunotherapeutic, and to methods of treatment of a human or animal subject comprising administration of a gonadotropin-releasing hormone in order to minimize the risk of progression of viral disease.

BACKGROUND OF THE INVENTION $CD4^+$ cells are key mediators of the immune response and are primary targets for HIV infection and related viral diseases. The current standard of care for HIV patients is antiretroviral therapy (ART), which are combinations of various antiretroviral (ARV) drugs that act in concert to suppress the HIV virus and attenuate disease progression. However, the long-term efficacy of ART is compromised by patient incompliance, drug toxicity and drug resistance. Thus, there is a great need in the art for new methods and means of increasing the immune competence of $CD4^+$ cells as well as other immune cells such as $CD8^+$ cells in patients suffering from HIV/AIDS or an immunologically related viral disease. In particular, there is a need for therapeutic options that minimize the risk of progression of disease, and for therapies that addresses the issue of patient incompliance by providing long-term, sustained, positive effects on the immune system.

DETAILED DESCRIPTION OF THE INVENTION

The present invention is based on the surprising finding that GnRH and analogues thereof may be used as adjuvant immunotherapeutics. Thus, short-term (about four weeks) treatment with a GnRH analogue provides long-term (36-48 months) and sustained immunomodulatory effects in HIV/AIDS patients. This minimizes the risk of long-term disease progression or provides a long-term prevention of progression of a viral disease.

It is contemplated that not only HIV patients will benefit from such treatment, but subjects in general suffering from a viral infection. The advantages of using a GnRH or an analogue thereof as an adjuvant immunotherapeutic includes better patient compliance, reduction of side effects as the treatment period is short and minimizing risk for developing ART resistance. At the same time, the immune response maintaining period is very long (3 years or more as seen from the examples).

GnRH I (also known as gonadotropin releasing hormone I or LHRH) is a decapeptide with the structure pyroGlu-His-Trp-Ser-Tyr-Gly-Leu-Arg-Pro-Gly-$NH_2$. It is produced as a 92 amino-acid propeptide that is modified post-translationally to form the final peptide with pyroglutamic acid at the amino terminus and a carboxamide at the carboxyl terminus. It is well-known that GnRH I is responsible for release of FSH and LH from the anterior pituitary gland, and it is normally released from the hypothalamus in a pulsative manner. Elevated supraphysiological levels of GnRH I induce an immediate increase of FSH and LH secretion via the GnRH I receptors of the anterior pituitary gland. However, this agonistic effect is soon followed by inhibition of FSH and LH secretion since high levels of GnRH I have an inherent antagonistic effect on the GnRH I receptors. Continuous administration of GnRH I at supraphysiological levels thus inhibits FSH/LH secretion and induces pharmacological castration (G. Fink. Gonadotropin Secretion and its Control. In *The Physiology of Reproduction*, 1998).

A large number of GnRH I analogues with agonist properties have been synthesized for use in various therapeutic areas. Initially, salts of GnRH I were used therapeutically (such as gonadorelin hydrochloride and gonadorelin diacetate tetrahydrate). Further drug discovery and development led to the clinical use of a wide variety of agents, including buserelin, triptorelin, nafarelin, histrelin and leuprorelin, each of which has improvements over gonadorelin such as extended half-life and super-agonism of the GnRH I receptor.

It has been reported that GnRH I not only exhibits hormonal effects but also may stimulate the immune system (Jacobson et al. *Endocrinology* 2004, 145 (1), pp. 330-336). McClean and McCluggage (McClean et al. *Int. J. Surg. Pathol.* 2003, 11 (4), pp. 339-344) observed massive infiltration of small mature lymphocytes in uterine leiomyomas after preoperative treatment with a GnRH I receptor agonist. Bardsley et al. (Bardsley et al. *Histopathology* 1998, 33 (1), pp. 80-82) made the same observation, indicating a stimulatory effect of GnRH I on migration of immune cells. Reports have been made on chronic plasma cell endometritis in hysterectomy specimens from HIV-infected women in a retrospective analysis (Kerr-Layton et al. *Infect. Dis. Obstet. Gynecol.* 1998, 6 (4), pp. 186-90), and on elevated (hypergonadotropic) FSH and LH levels in HIV-infected men (Arver et al. *J. Androl.* 1999, 20 (5), pp. 611-618; Brookmeyer et al. *Horm. Res.* 2000, 54 (5-6), pp. 294-295). By administering GnRH I to diabetes-prone BB rats exhibiting an AIDS-like lymphocyte profile, the $CD4^+$ T-lymphocyte numbers was increased (Jacobson et al. *J. Allergy Clin. Immunol.* 1999, 104, 653-658).

Recently, a second form of GnRH, named GnRH II (pyroGlu-His-Trp-Ser-His-Gly-Trp-Tyr-Pro-Gly-$NH_2$, differences from GnRH I underlined for clarity) has been shown to exist in humans. GnRH II is a non-hypothalamic form primarily produced outside the brain, and it has been suggested to be involved in the non-endocrine aspects of the GnRH system (White et al. *PNAS* 1998, 95 (1), pp. 305-309). GnRH II stimulates MHC class I expression on T cells, suggesting that GnRH II directly activates these cells (unpublished data). Moreover, evidence suggest that a gene encoding a GnRH II receptor is present on human chromosome 1q12, and that the GnRH II receptor is expressed on T cells, since these cells respond to GnRH stimulation by increasing MHC class I expression (unpublished data). In addition, qPCR analysis indicates that GnRH II receptor mRNA is expressed in T cells, and that the relative expression levels of GnRH II receptor mRNA are increased compared to GnRH I receptor mRNA in both naive and memory T cells (unpublished data.

WO 2009/145690 A1 describes that administration of a supraphysiological castrating amount of GnRH I or a GnRH I analogue may result in a maintained or increased immune competence in T-cell deficient patients such as patients suffering from HIV/AIDS. In this context, it is very likely that GnRH I or the GnRH I analogue in addition to its endocrine effects cross-signals and stimulates the immune system by binding to the GnRH II receptor on T cells when supraphysiological castrating levels of GnRH or a GnRH I analogue are used. To attenuate or eliminate any endocrine side effects, GnRH I or the GnRH I analogue may be administered together with one or more natural, semi-synthetic or synthetic sex hormones.

However, it is contemplated that by using GnRH II or a GnRH II analogue in the treatment of HIV/AIDS or other related viral diseases, the negative endocrine effects observed with GnRH I and GnRH I analogues may be minimized and the positive immunomodulatory effects may be enhanced.

As can be seen from the examples herein, an open-label phase II clinical study in HIV-infected antiretroviral therapy (ART) naïve male patients (n=26) investigating the effect of administration of buserelin acetate for 28 days (1.2 mg/day) resulted in several positive GnRH I-mediated effects on the immune system. Treatment provided a decrease in HIV viral load, an increase in HLA class I molecules on $CD4^+$ T cells, an increase in the number of HIV specific binding sites on $CD8^+$ T cells, and an increase in activation of $CD4^+$ and $CD8^+$ T cells. Moreover, no serious adverse events were recorded during the study period, and the treatment was deemed safe and well-tolerated.

Importantly, and most surprisingly, a follow-up study conducted 36-48 months after end of the treatment period revealed the positive immunological effects to be sustained, indicating that treatment with a GnRH analogue for only four weeks is able to prevent HIV/AIDS disease progression for at least three years after treatment, in some cases for up to four years and, perhaps, even longer. For about 33-50% of all subjects included in the follow-up study no progression in viral count or decrease in $CD4^+$ cell counts was observed. These results indicate that subjects may still have the virus, but there is no remission of the viral disease and no progression into AIDS. In the present context, the term "cure" is meant to include such situations (i.e. subjects still have the virus, but no disease symptoms are observed).

In the follow-up study, disease progression was based on immunological criteria and defined as a medical condition in which a patient had experienced any AIDS-defining disease such as tuberculosis infection during the time period from the last day of treatment in the clinical trial until the day of follow up, or whose $CD4^+$ T cell count measured in whole blood had decreased by more than 50 cells/µl to a value below 500 cells/µl. In an interim analysis of 13 out of 26 patients, nine patients were subject to full clinical evaluation. Of these nine patients, six patients (corresponding to 66.7%) demonstrated no immunological disease progression. In these patients, the long-term effects of treatment included sustained immunological activation of $CD4^+/CD8^+$ cells (resembling normal physiological levels), no increase in viral load, and no clinical progression of HIV. This finding shows that short-term treatment of HIV patients with a GnRH analogue provides long-term, sustained, vaccine-like effects on the immune system that minimizes the risk of disease progression. In the present study, a single testosterone cypionate depot injection (150 mg) was administered as part of the treatment to compensate for any endocrine side effects. However, the GnRH analogue is contemplated to provide the beneficial effects on the immune system. Thus, in one aspect, the present invention relates to the use of a GnRH analogue for use in minimizing the risk of progression of a viral disease.

The GnRH analogue of the present invention may be one or more agents selected from GnRH I, a GnRH I analogue, GnRH II, a GnRH II analogue, or any pharmaceutically acceptable salt thereof. GnRH analogues useful in the invention comprise but are not limited to deslorelin, avorelin, leuprorelin (also known as leuprolide), triptorelin, buserelin, fertirelin, lutrelin, goserelin, historelin and nafarelin. Of further interest are GnRH analogues selected from triptorelin, buserelin, leuprorelin, nafarelin, histrelin, and goserelin. Of even further interest are GnRH analogues selected from buserelin, triptorelin, and goserelin. Of particular interest is buserelin or any pharmaceutically acceptable salt thereof such as buserelin acetate.

In view of the indications of a human GnRH II receptor seen by the present inventors (unpublished data), it may be contemplated that by using GnRH II or a GnRH II analogue in the treatment of HIV/AIDS or other related viral diseases, the negative endocrine effects observed with GnRH I and GnRH I analogues may be minimized and the positive immunomodulatory effects may be the same or even enhanced. Thus, also of particular interest in the context of the invention are GnRH II, GnRH II analogues or a pharmaceutical salt thereof. These analogues may exhibit no or markedly reduced negative endocrine effects compared with the side effects observed with administration of GnRH I or GnRH I analogues.

The GnRH analogue of the present invention is useful for minimizing the risk of any viral disease such as but not limited to Adenovirus Infection, Alphavirus Infection, Arbovirus Encephalitis, Borna Disease, Bunyavirus Infection, Calicivirus Infection, Chickenpox, Condyloma Acuminata, Coronavirus Infection, Coxsackievirus Infection, Cytomegalovirus Infection, Dengue fever, Contagious Ecthyma, Epstein-Barr Virus Infection, Erythema Infectiosum, Hantavirus Infection, Viral Hemorrhagic Fever, Viral Hepatitis, Herpes Simplex, Herpes Zoster, Infectious Mononucleosis, Influenza, Lassa Fever, Measles, Molluscum Contagiosum, Mumps, Paramyxovirus Infection, Phlebotomus Fever, Polyomavirus Infection, Rabies, Respiratory Syncytial Virus Infection, Rift Valley Fever, Rubella, Slow Virus Diseases, Smallpox, Subacute Sclerosing Panencephalitis, Tumor Virus Infections, West Nile Fever, Yellow Fever and HIV/AIDS. As demonstrated in the examples, GnRH analogue is particularly useful as an adjuvant immunotherapeutic, whereby it minimizes the risk of progression of HIV/AIDS.

In order to exert its positive therapeutic effects on the immune system, the GnRH analogue of the invention should be administered in an amount sufficient for maintaining an elevated plasma level (compared to normal level). This elevated level normally induces castration. The dosage regimen of the GnRH analogue may be varied according to its pharmaceutical properties. The GnRH analogue may be administered by any route of administration such as oral, topical, mucosal, pulmonary, parenteral, sublingual, nasal, ocular and enteral administration. As seen from the examples herein a suitable dose is equivalent to the dosage regimes normally recommended for the GnRH or GnRH analogues (recommended for prostate cancer).

Of particular interest to the present invention are suitable pharmaceutical compositions containing a GnRH analogue, in particular a slow release or depot composition. Examples of such formulations include Zoladex® (goserelin acetate injection) and Decepeptyl-Depot® 20 (triptorelin pamoate injection). A suitable dosage regimen of Zoladex® comprises subcutaneous injection of a dose equivalent of 3.6 mg goserelin into the anterior abdominal wall to provide effective suppression of estradiol or testosterone for 28 days. Another suitable dosage regimen of Zoladex® comprises subcutaneous injection of 10.8 mg every 12th week. A suitable dosage regimen of Decapeptyl-Depot® 20 comprises intramuscular injection of 3.75 mg or 11.25 mg to effectively provide suppression of FSH and LH release during four or twelve weeks, respectively. Further relevant examples of slow or sustained release formulations can be found in the literature and are within the scope of the present invention. Other pharmaceutical compositions of interest include Suprefact® (buserelin acetate nasal spray). A suitable dosage regimen of Suprefact® comprises intranasal administration of 1.2 mg/day for 28 days.

The above-mentioned suitable pharmaceutical compositions as well as other suitable pharmaceutical compositions of the invention are listed in Table 1. However, other pharmaceutical compositions comprising GnRH analogues as well as other dosage regimens than those mentioned in here are also within the scope of the present invention.

TABLE 1

Pharmaceutical compositions

| Name of compound | Relevant Dose | Dosage regimen |
|---|---|---|
| Buserelin acetate nasal spray solution (Suprefact ®) | 0.75-2 mg/day such as 1.2 mg/day (4 × 300 µg) | 2 × 150 µg QID for 28 days |
| Triptorelin acetate injection suspension (Decapeptyl-Depot ® and Gonapeptyl-Depot ®) | 2-5 mg/month such as 3.75 mg/month | 3.75 mg/month for 6 months |
| Triptorelin acetate injection suspension depot (Moapar ®) | 7-15 mg/12 weeks such as 11.25 mg/12 weeks | 11.25 mg/every 12 weeks for 6 months |
| Buserelin acetate implant (Suprefact-Depot ®) | 5-15 mg/12 weeks such as 9.45 mg/12 weeks | 9.45 mg/every 12 weeks for 6 months |
| Goserelin acetate injection suspension depot subcutaneous or intramuscular (Zoladex ®) | 2-15 mg every month, every second month or every 12 weeks such as 3.6 mg/month or 10.8 mg/12 weeks | 3.6 mg/month for 6 month or 10.8 mg/12 weeks for 6 months |
| Deslorelin, deslorelin acetate (Ovuplant ®, Suprelorin ® or Sucromate Equine ® approved for veterinary use) | 250-500 µg/kg body weight subcutaneously, daily over 2 years or 20-100 µg subcutaneously daily for up to 10 weeks | 250-500 µg/kg body weight subcutaneously, daily over 2 years or 20-100 µg subcutaneously daily for up to 10 weeks |
| Avorelin | 5-25 mg with 6 months interval such as 10 or 15 mg subcutaneously as a depot formulation with 6 months interval | 10 or 15 mg subcutaneously as a depot formulation with 6 months interval |
| Leuprorelin (leuprolide) (Lupron ®, Lupron Depot ®, Viadur ®, Eligard ®, Leupromer ®) | Dependent on the formulation type 2-25 mg every 1-4 months such as 3.75 mg, 7.5 mg, 11.25 mg or 15 mg as a depot formulation for intramuscular injection every 3 or 4 months; 72 mg yearly as a subcutaneous implant; 7.5 mg for monthly subcutaneous depot injection | 3.75 mg, 7.5 mg, 11.25 mg or 15 mg as a depot formulation for intramuscular injection every 3 or 4 months; 72 mg yearly as a subcutaneous implant; 7.5 mg for monthly subcutaneous depot injection |
| Fertirelin | | |
| Lutrelin | | |
| Historelin | 250-500 µg/kg body weight subcutaneously, daily over 2 years or 20-100 µg subcutaneously daily for up to 10 weeks | 250-500 µg/kg body weight subcutaneously, daily over 2 years or 20-100 µg subcutaneously daily for up to 10 weeks |
| Nafarelin, nasal spray (Synarela ®) | 100-1000 µg daily for 3-6 months such as 200 µg 2 times daily for 6 months or 200 µg 3 times daily for 3 months | 200 µg 2 times daily for 6 months or 200 µg 3 times daily for 3 months |

To compensate for any unwanted endocrine side effects associated with administration of supraphysiological, in particular castrating, levels of a GnRH or GnRH analogue, the GnRH analogue may be co-administered with one or more sex hormones to provide hormonal substitution. Sex hormones (also known as sexual hormones, sex steroids or gonadal steroids) of the present invention comprises one or more natural, semi-synthetic or synthetic sex hormones or any pharmaceutically acceptable salt thereof.

In a male person, the sex hormones include androgens such as testosterone or an agent exhibiting corresponding physiological effects, including agents selected from dihydrotestosterone, androsterone, dehydroepiandrosterone (DHEA), dehydroepiandrosterone (DHEA-S), androstenedione, methyltestosterone, and stanozolol. Androgens of particular interest comprise testosterone, methyltestosterone, and stanozolol.

In a female person, the sex hormones include estrogens such as estrogen or an agent exhibiting corresponding physiological effects, optionally in combination with a gestagen such as progesterone or an agent exhibiting corresponding physiological effects. Suitable estrogens may be selected from estrogen, estradiol, estriol, estrone, ethynylestradiol, mestranol, dinestrol, and diethylstilbestrol, and conjugated estrogens such as but not limited to estrone sulphate, equilin sulfate, equilenin sulfate, 17α-dihydroequilin sulfate, 17α-estradiol sulfate, and 8,9-dehydroestrone. Suitable gestagens may be selected from progesterone or analogs thereof such as hydroxyprogesterone caproate, medroxyprogesterone acetate, norethisterone acetate, megestrol acetate, medrogestone, and norgestrel. Estrogens of particular interest comprise estrogen, estradiol, conjugated estrogens, ethynylestradiol, mestranol, dinestrol, and diethylstilbestrol, whereas gestagens of particular interest comprise progesterone, hydroxyprogesterone caproate, medroxyprogesterone acetate, norethisterone acetate, megestrol acetate, medrogestone, and norgestrel.

To compensate for any reproductive side effects associated with administration of an unphysiological amount of a GnRH analogue, the one or more natural, semi-synthetic or synthetic sex hormones of the invention may be administered in an amount sufficient to compensate for the castration effect of the GnRH analogue. The dosage regimen of the one or more sex hormones may be varied according to their pharmaceutical properties. The one or more sex hormones may be administered by any route of administration such as oral, topical, mucosal, pulmonary, parenteral, sublingual, nasal, ocular and enteral administration.

In cases of co-administration of a GnRH analogue and one or more sex hormones to provide hormonal substitution, it is preferred that a period of overlap exists wherein administration of the GnRH analogue substantially overlaps the period of hormonal substitution, such as by 50% or more, preferably by 75% or more, more preferably by 85% or more, more preferably by 90% or more, and even more preferably by 95% or more. According to the present invention, a period of overlap refers to a period of time in which the plasma levels of both the GnRH analogue and the sex hormone are sufficient to elicit the desired pharmacological effects. In those cases where GnRH I or a GnRH I analogue is used, addition of sex hormone substitution is advantageous to increase compliance and serves as a rescue of side effects i.e. steroid hormone depletion after introduction of GnRH treatment. The two treatment regimens (GnRH and sex hormone) should therefore overlap during the course of treatment.

It is contemplated that GnRH analogues without any endocrine side effects or only with minor endocrine side effects—such as but not limited to GnRH II or GnRH II analogues—may be developed and used as an alternative to the combination of GnRH I or a GnRH I analogue and one or more sex hormones. Such GnRH analogues with no or minor negative endocrine effects are within the scope of the present invention. The dosage regimen may be varied according to the GnRH analogues and their pharmaceutical properties, and they may be administered by any route of administration such as oral, topical, mucosal, pulmonary, parenteral, sublingual, nasal, ocular and enteral administration.

In another aspect, the present invention relates to pharmaceutical compositions comprising a GnRH analogue and, optionally, one or more sex hormones and one or more pharmaceutically or veterinary acceptable excipients for use in minimizing the risk of progression of viral disease. When GnRH I, a GnRH I analogue or a GnRH II analogue (with endocrine side effects) is employed, the dosage regimen normally includes the use of one or more sex hormones.

For such compositions, the GnRH analogue may be selected from GnRH I, GnRH I analogues such as but not limited to deslorelin, avorelin, leuprorelin, triptorelin, buserelin, fertirelin, lutrelin, goserelin, historelin, and nafarelin, GnRH II, GnRH II analogues, or any pharmaceutically acceptable salts thereof.

For such compositions for use in male subjects, the sex hormone may be selected from androgens such as testosterone or an agent exhibiting corresponding physiological effects, such as but not limited to agents selected from dihydrotestosterone, androsterone, dehydroepiandrosterone (DHEA), dehydroepiandrosterone (DHEA-S), androstenedione, methyltestosterone, stanozolol, or any pharmaceutically acceptable salts thereof.

For such compositions for use in female subjects, the sex hormone may be selected from estrogen or an agent exhibiting corresponding physiological effects, such as but not limited to estrogen, estradiol, estriol, estrone, ethynylestradiol, mestranol, dinestrol, and diethylstilbestrol, and conjugated estrogens such as but not limited to estrone sulphate, equilin sulfate, equilenin sulfate, 17α-dihydroequilin sulfate, 17α-estradiol sulfate, and 8,9-dehydroestrone, or any pharmaceutically acceptable salts thereof.

Compositions for use in female subjects patients may optionally also contain a gestagen selected from progesterone or an agent exhibiting corresponding physiological effects such as hydroxyprogesterone caproate, medroxyprogesterone acetate, norethisterone acetate, megestrol acetate, medrogestone, norgestrel, or any pharmaceutically acceptable salts thereof.

A person skilled in pharmaceutical formulation will know how to formulate specific compositions e.g. with guidance from Remington's Pharmaceutical Sciences, 18th edition, Mack Publishing Company, 1990, or a newer edition.

In another aspect, the present invention relates to pharmaceutical kits for use in minimizing the risk of progression of viral disease comprising, in a single package, a first composition comprising an suraphysiological, in particular a castrating amount of a GnRH analogue, optionally a second composition comprising a castration attenuating or eliminating amount of one or more natural, semi-synthetic or synthetic sex hormones, and instructions for use. The first and second composition may be designed for different or the same dosage regimen, and the instructions contain a description of the dosage regimen.

For such pharmaceutical kits, the GnRH analogue may be selected from GnRH I, GnRH I analogues such as but not limited to deslorelin, avorelin, leuprorelin, triptorelin, buserelin, fertirelin, lutrelin, goserelin, historelin, and nafarelin, GnRH II, GnRH II analogues, or any pharmaceutically acceptable salts thereof.

For such pharmaceutical kits for use in male subjects, the sex hormone may be selected from androgens such as testosterone or an agent exhibiting corresponding physiological effects, such as agents, but not limited to, selected from dihydrotestosterone, androsterone, dehydroepiandrosterone (DHEA), dehydroepiandrosterone (DHEA-S), androstenedione, methyltestosterone, stanozolol, or any pharmaceutically acceptable salts thereof.

For such pharmaceutical kits for use in female subjects, the sex hormone may be selected from estrogen or an agent exhibiting corresponding physiological effects, such as but not limited to estrogen, estradiol, estriol, estrone, ethynylestradiol, mestranol, dinestrol, and diethylstilbestrol, and conjugated estrogens such as but not limited to estrone sulphate, equilin sulfate, equilenin sulfate, 17α-dihydroequilin sulfate, 17α-estradiol sulfate, and 8,9-dehydroestrone, or any pharmaceutically acceptable salts thereof.

Pharmaceutical kits for use in female subjects may optionally also comprise a third composition comprising a gestagen selected from progesterone or an agent exhibiting corresponding physiological effects such as but not limited to hydroxyprogesterone caproate, medroxyprogesterone acetate, norethisterone acetate, megestrol acetate, medrogestone, norgestrel, or any pharmaceutically acceptable salts thereof.

In another aspect, the present invention relates to a method for minimizing the risk of progression of a viral disease, in particular HIV/AIDS, the method comprising
i) administering to a human or animal subject a therapeutically effective amount a GnRH analogue or any pharmaceutically acceptable salt thereof, and
ii) optionally administering one or more natural, semi-synthetic or synthetic sex hormones in an amount sufficient to compensate for any negative endocrine effects caused by the GnRH analogue.

In case of GnRH I or a GnRH I analogue, the amount should normally be such that it is sufficient for maintaining in the subject an elevated supraphysiological plasma level, in particular, a castrating plasma level.

A condition for obtaining long-term protective effects and minimizing the risk of disease progression is that the subject is or has been infected with the virus in question. Thus, a method of the invention may comprise
i) testing a biological sample from a subject for presence of a specific virus,
ii) if the virus is or has been present, treating the subject with a GnRH analogue in accordance with a suitable dosage regimen such as one of those described herein,
iii) optionally, co-treating the subject with one or more sex hormones to minimize the risk of endocrine side effects,
iv) optionally, subjecting the subject to a follow-up examination to determine the level of CD4 and/or CD8 cells, viral load, and/or any signs of progression of disease.
Step iv) is normally included in order to secure correct treatment of the subject in case the disease is in remission.

Definitions

The articles "a", "an", and "the" are used herein to refer to one or to more than one (i.e. at least one) of the grammatical objects of the article. By way of example, "an analogue" means one analogue or more than one analogue.

Unless otherwise stated, the term "GnRH analogue" refers to one or more of GnRH I, an analogue of GnRH I, GnRH II, an analogue of GnRH II, or any pharmaceutical salts thereof. GnRH I or a GnRH I analogue predominantly has i) stimulating effect on or ii) affinity for GnRH I receptor, whereas GnRH II or a GnRH II analogue may have i) stimulating effect on or ii) affinity for another receptor, which may be a GnRH II receptor. Thus, GnRH I or a GnRH I analogue may stimulate or have affinity for the GnRH II receptor as well, but to a much lesser extent. Likewise, GnRH II or a GnRH II analogue may stimulate or have affinity for the GnRH I receptor as well, but to a much lesser extent. The stimulating/binding of the GnRH I and/or GnRH II receptor by GnRH analogues can be studied as described in the Experimental section.

Figure 1:
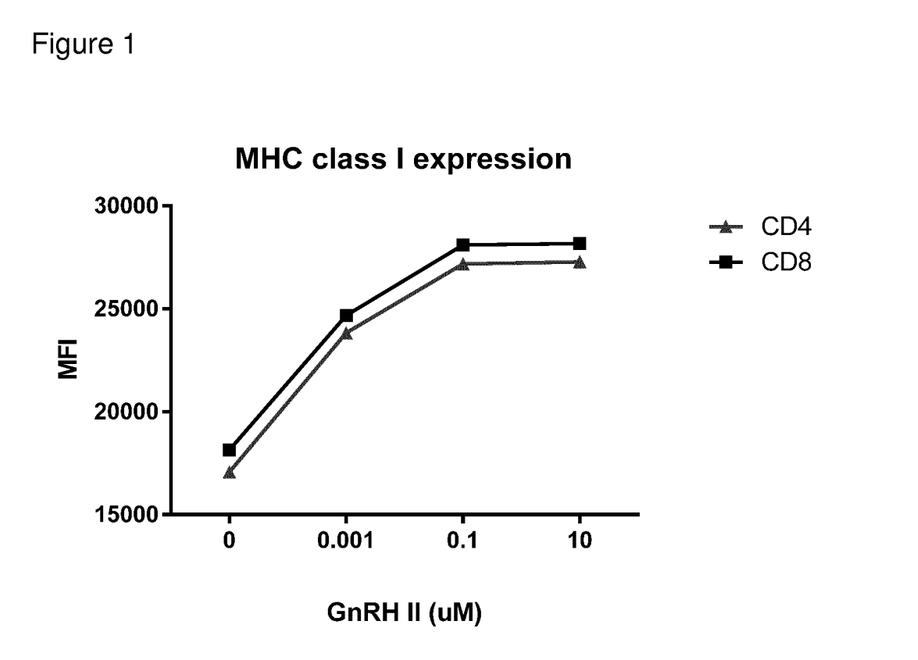
FIG. 1: Expression of MHC class I after stimulation of T cells with increasing concentrations of GnRH II. PBMCs from a healthy donor was stimulated with GnRH II and IL-2 for 72 hours. Data points represent mean fluorescent intensity of MCH class I expression on $CD4^+$ T cells (blue triangles) or $CD8^+$ T cells (black squares) measured with flow cytometry.
Figure 2:
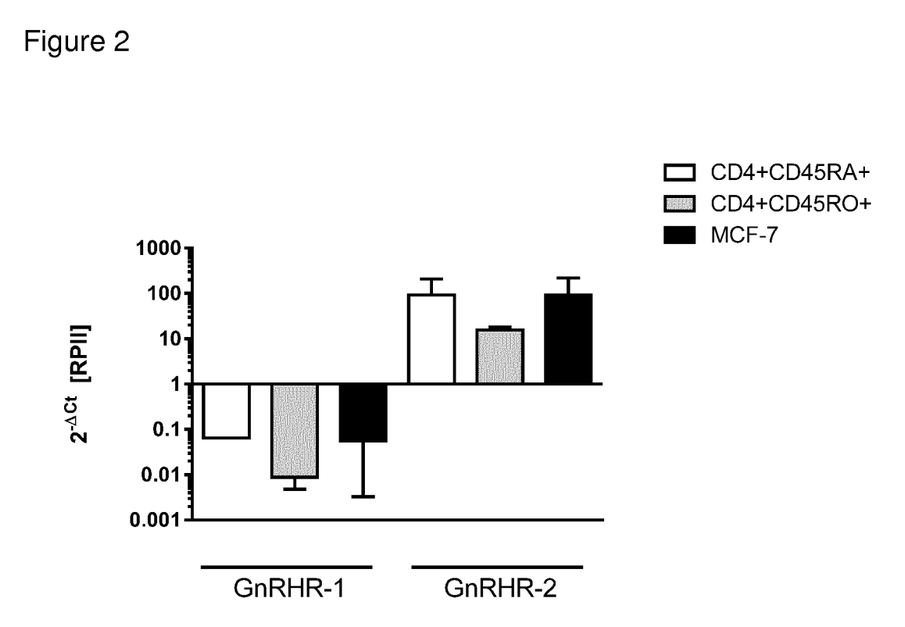
FIG. 2: GnRH receptor expression in human T cells analysed with quantitative realtime PCR. The bars represent ratios of GnRHR I or GnRHR II mRNA normalized to RNA polymerase II expression in sorted naive T cells (white bars) or memory T cells (gray bars). MCF-7 breast cancer cell line (black bar) was used as a positive control.

Unlike in other mammals, only one conventional human GnRH receptor has been described, the type I GnRH receptor. The type II GnRH receptor homologue is present on chromosome 1q12 gene in humans but contains a frame shift and a stop codon and is believed not to be functionally expressed. Surprisingly, our findings suggest that the type II GnRH receptor is indeed expressed on T cells as they respond to GnRH stimulation by increased MHC class I expression (FIG. 1). These functional findings were substantiated by qPCR analysis where we could demonstrate expression of the type II GnRH receptor mRNA. In addition, the relative expression level of the type II GnRH receptor was higher compared to the expression levels of the type I GnRH receptor on naive and memory T cells (FIG. 2). Thus, we have identified that the expression of the type II GnRH receptor is the dominant receptor expressed on T cells, functionally responsive to GnRH stimulus.

We have also discovered that GnRH I analogs may activate T cells leading to MHC class I expression. In a recent clinical trial using the GnRH I analog Buserelin as treatment for HIV, HIV infected men were provided with sex hormone substitution to minimize the endocrine effects of GnRH I. These effects are mediated by GnRH I binding to pituitary type I GnRH receptors, causing decreased testosterone production and subsequently impotence. It is very likely that GnRH I in addition to its endocrine effects cross-signal and stimulate the immune system by binding to the type II GnRH receptor on T cells when high castrating levels of GnRH analogues are used. Interestingly, GnRH I binding to receptors expressed in breast cancer cells displays a low binding affinity (Kd, 1.6-3.0×10(−6) M), whereas central pituitary binding of GnRH I displays a 1000-fold higher affinity (Kd, 4.8×10(−9) M) (11).

It is likely that the difference in binding affinity of GnRH I and GnRH II peptides reflects the expression of type I GnRH receptors specialized for GnRH I binding on pituitary cells, whereas peripheral cells may have dominated expression of type II GnRH receptor and therefore low affinity and an "off target" effect of GnRH I binding. Thus, our unexpected finding that the type II GnRH receptor is the dominating receptor on T cells is novel and may explain the receptor physiology of GnRH I and GnRH II. Therefore, by using GnRH II-like peptides in the treatment of HIV the endocrine effect should be minimized and the immune stimulation effect isolated and enhanced.

The term "adjuvant immunotherapeutic" as used herein is intended to denote a substance that is capable of inducing an immunological response directed against a viral infection. Thus, the adjuvant immunotherapeutic is not in itself subject to an immunologic response, but acts as an inducer.

As used herein, the time period indicated for the effect of the adjuvant immunotherapeutic may start at the same time as treatment with the adjuvant immunotherapeutic initiates.

The term "treatment period" is intended to denote the time period, wherein treatment takes place. As an example, the treatment period in example 1 is 4 weeks.

The term "immune response maintaining period" is intended to denote the time period, where an effect of an immune response is observed. An effect of an immune response can be observed by measurement of one or more of HIV-1bDNA (relevant for infection with HIV-1), viral load $CD4^+$, $CD8^+$, $CD4^+/CD8^+$, $CD4^+$ HLA ABC MFI, $CD8^+$ tetramer MFI etc.

The pharmaceutically acceptable salts of the compounds of the invention include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, cypionic, formic, lactic, maleic, tartaric, citric, palmoic, malonic, caproic, hydroxymaleic, phenylacetic, glutamic, benzoic, salicylic, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The term 'supraphysiological' mentioned in relation to plasma level, amount, and dosage of a GnRH or analogue thereof is defined according to Tayler et al. (J. Fertil. Steril. 2010, 93 (5), pp. 1668-1675) and is to be understood as a level, amount, or dosage of a GnRH analogue that in a subject leads to a stable and high plasma concentration of the GnRH analogue, causing the pulsative secretion pattern of endogenous GnRH to be attenuated or eliminated.

EXPERIMENTAL

GnRH I vs GnRH II Assay

Compounds are tested on cells made to express either GnRH I receptors or GnRH II receptors by transfection. The cells are exposed to labelled GnRH compound, washed and then assessed by measuring the label on the cells. The label is either measured directly (radioactive isotope label or fluorescent label) or indirectly (biotin labelled peptide).

Signalling induced by the GnRH compounds is measured in the cell lines expressing either GnRH I receptors or GnRH II receptors. GnRH compounds are investigated for their respective affinity to GnRH I receptors and GnRH II receptors using competition assays. Calcium flux is measured using cells labelled with Fluo-4-Direct either using a flow cytometer or by live cell imaging microscopy, in order to evaluate their potency establishing ED50 values. Signalling is also studied by western blotting using antibodies to p-ERK or p-JNK.

To assess the effects of cellular activation on the production of LH and FSH and compare it with stimulation of immune related functions, the effects of the compounds are studied on pituitary cells and immune cells expressing either GnRH I receptors or GnRH II receptors.

EXAMPLES

Example 1: Open-Label Phase II Clinical Study

Figure 3:
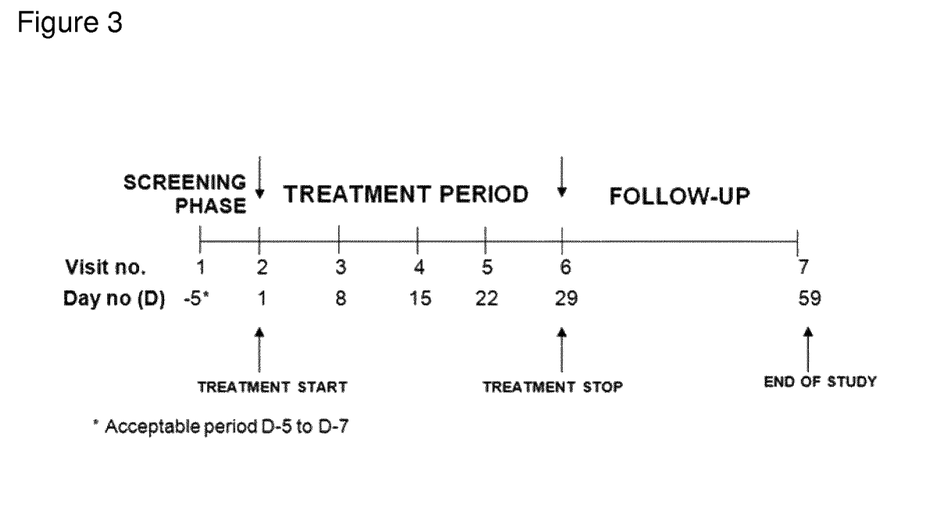
FIG. 3. Study outline and visit schedule of phase IIa clinical study.

An open-label, uncontrolled, single-center phase IIa clinical study was conducted at the Clinical Research Unit at the University of Pretoria, South Africa. The study outline is depicted in FIG. 3. The subjects were HIV 1-infected antiretroviral therapy (ART) naïve male patients (n=26). The inclusion criteria were asymptomatic verified HIV-1 infection as documented by HIV antibody test, male gender, age of 18-50 years, $CD4^+$ T cell count of >350 cells/μl whole blood, and HLA-A*0205, HLA-A*3002, or HLA-B*1503 haplotype positivity. The patients received 1.2 mg/day (4×300 μg, each time administered as 150 μg into each nostril) of buserelin acetate nasal spray solution (Supretact®, Sanofi-Aventis) for 28 days. To compensate for any endocrine side effects, the patients further received a single intramuscular injection of 150 mg testosterone cypionate (Depo®-Testosterone, Pfizer) at day 7 of the treatment period. The primary study objective was to evaluate the safety and tolerability of intranasal administration of buserelin acetate for 28 days, and the secondary study objectives were to evaluate the effects on T cell populations, HIV viral load and serum concentrations of FSH, LH and testosterone.

In terms of safety, no serious adverse events (SAEs) occurred during the study, and no patients experienced intolerable adverse events causing treatment withdrawal. All adverse events except one was graded as mild, and the great majority of the events were considered as unrelated to treatment. A summary of the adverse events is provided in Table 2.

TABLE 2

Summary of adverse events (AE) in phase IIa study

| Type of event | Safety (n = 26) |
|---|---|
| Any AE | 26 (100.0%) |
| Any SAE | 0 (0.0%) |
| Any treatment-related AE | 17 (65.4%) |
| Any treatment-related SAE | 0 (0.0%) |
| Any AE leading to discontinuation | 1 (3.8%) |
| Any AE affecting impotence | 6 (23.1%) |
| Any AE affecting libido | 8 (30.8%) |
| Death | 0.0% |

For categorical variable, n (%) is presented

In terms of efficacy, the HIV viral load decreased between baseline and visit 6 (end of treatment) and visit 7 (follow-up), respectively, with the viral load reduction observed at visit 7 being more pronounced than the reduction observed at visit 6. Also, HLA class I molecules on $CD4^+$ T cells increased between baseline and visit 6, and the number of HIV-specific binding sites on $CD4^+$ T cells (CD8 tetramer MFI) at visit 7 was significantly greater compared to baseline. Moreover, a detailed analysis of 16 immunological variables indicated that the treatment resulted in activation of $CD4^+$ and $CD8^+$ T cells.

Figure 4:
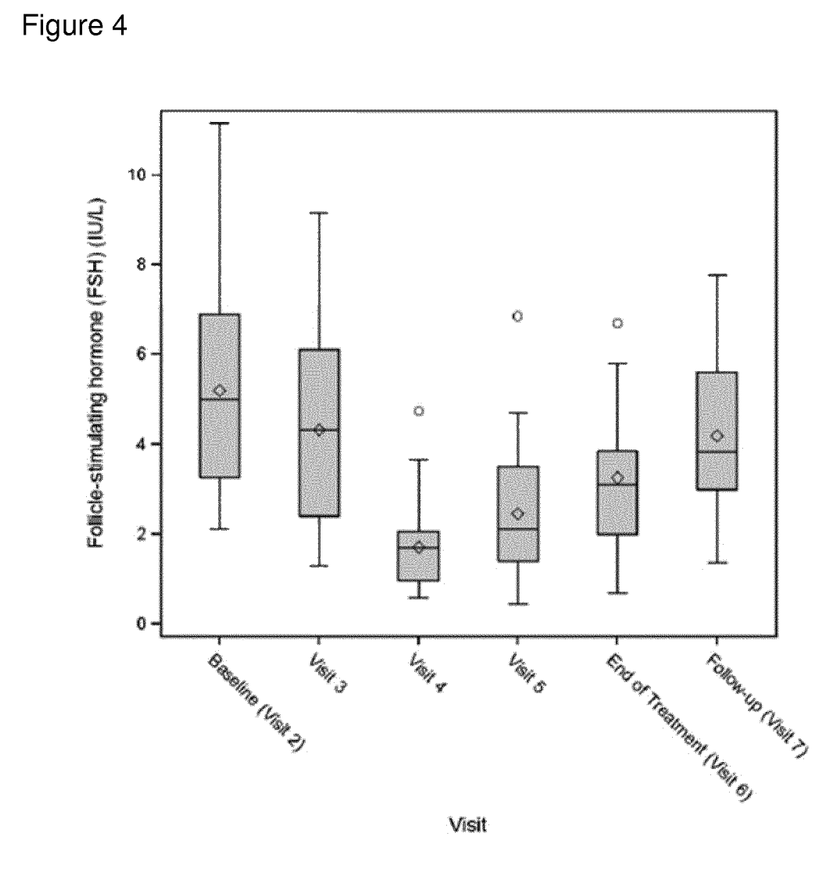
FIG. 4: FSH levels of the 26 patients as measured during the visits of the phase IIa clinical study.
Figure 5:
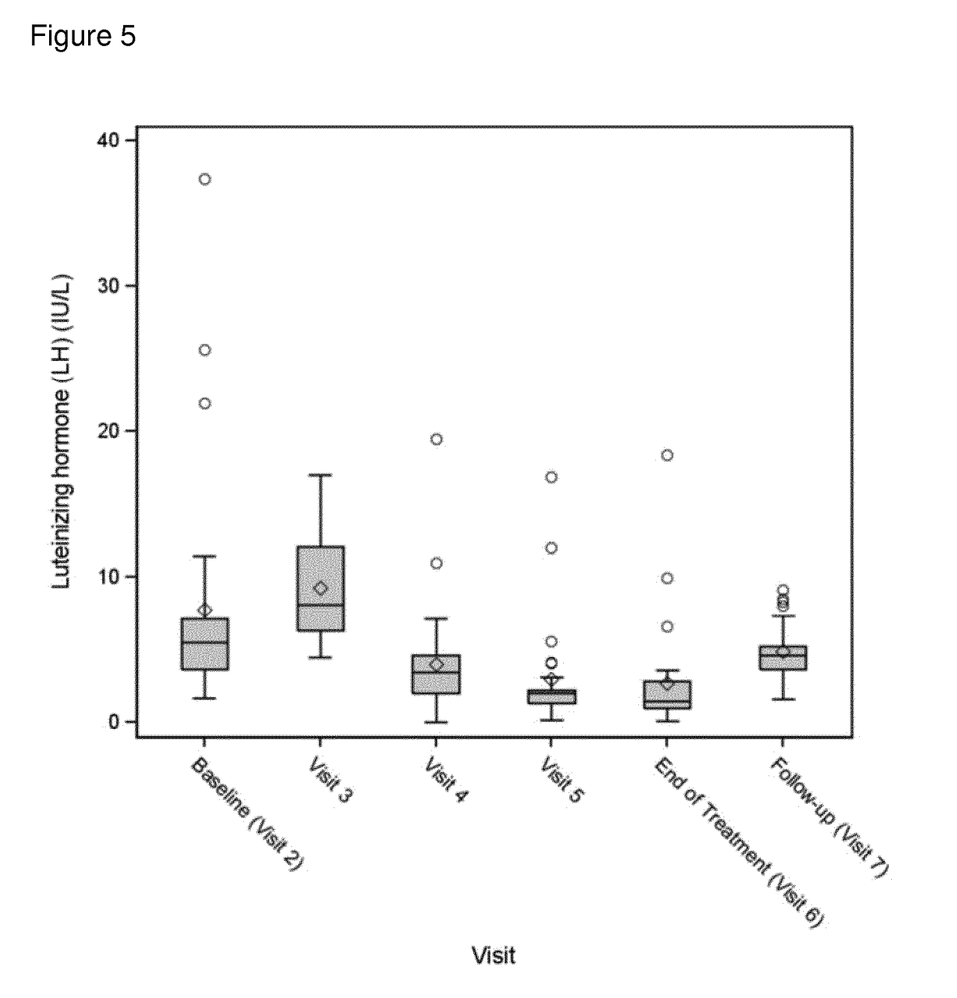
FIG. 5: LH levels of the 26 patients as measured during the visits of the phase IIa clinical study.
Figure 6:
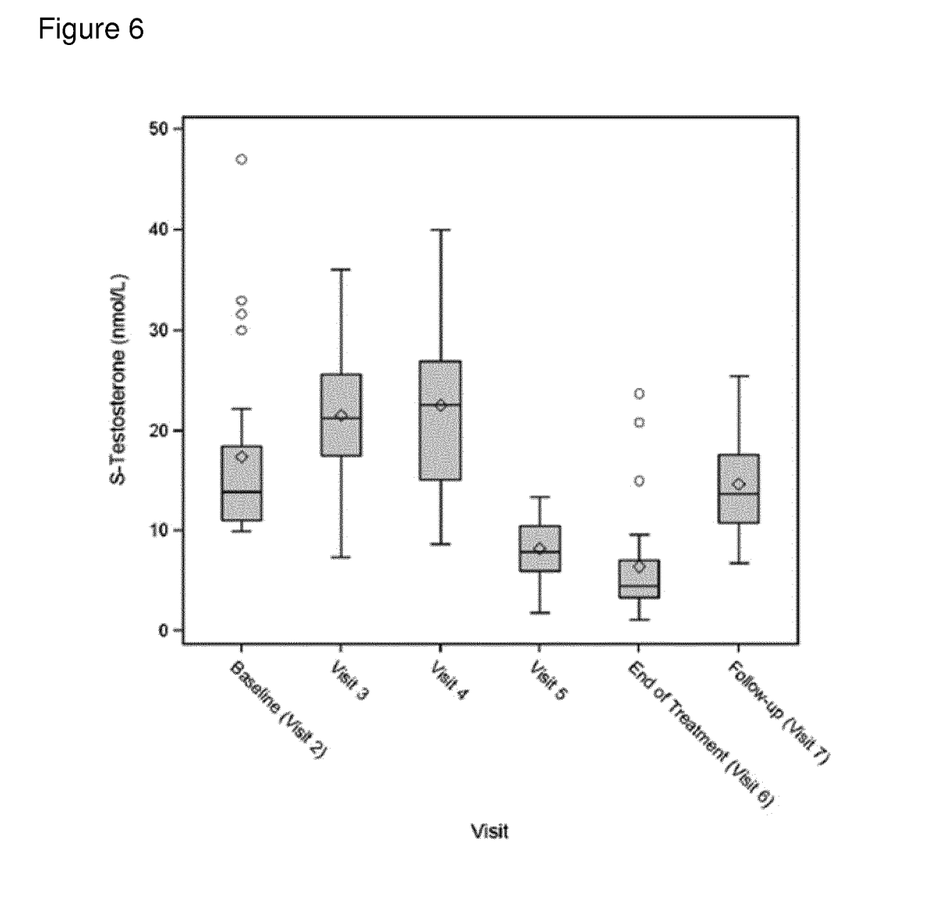
FIG. 6: Testosterone levels of the 26 patients as measured during the visits of the phase IIa clinical study.

As expected, the serum levels of FSH, LH and endogenous testosterone decreased during the treatment period, but had recovered at the time of the follow-up visit (FIGS. 4-6).

Example 2: Follow-Up Study and Interim Analysis

To investigate the long-term effects of GnRH treatment in patients suffering from HIV/AIDS, in particular with the intend of developing means to minimize the risk of disease progression, a follow-up study and interim analysis was conducted 36-48 months after the open-label phase II clinical study. The aim of the study was to assess progression of the HIV infection during the time period from completion of the phase IIa clinical study (Example 1), based on an assessment of the past and current clinical, immunological and virological status.

The follow-up included 13 out of the original 26 patients, of which nine patients were subject to full clinical examination. For the interim analysis, disease progression was based on immunological criteria and defined as a medical condition in which a patient had experienced any AIDS-defining disease such as tuberculosis infection during the time period from the last day of treatment in the clinical trial until the day of follow up, or whose $CD4^+$ T cell count measured in whole blood had decreased by more than 50 cells/µl to a value below 500 cells/µl. The interim analysis revealed that six out of the nine patients subjected to full evaluation demonstrated no immunological disease progression. In these patients, the long-term effects of treatment included sustained immunological activation of $CD4^+/CD8^+$ cells (resembling normal physiological levels), no increase in viral load, and no clinical progression of HIV.

A summary of the findings of the 13 patients included in the follow up study is provided below:

History of start of ART treatment after initial GnRH treatment: seven of the 13 patients (54%) had started ART treatment by the time of reevaluation (36-48 months after the phase IIa study—Example 1).

History of HIV-associated diseases (AIDS defining diseases including TB): two of the 13 patients (15%) had a history of pulmonary TB without dissemination since completion of the phase IIa study. The TB cases were treated successfully. No other events or severe diseases were reported by the reviewed patients or were seen at the follow-up examination after 36-48 months.

Immunological status 36-48 months after initial GnRH treatment: To assess the immunological status, the last $CD4^+$ T cell count results of the initial clinical study at visit 6 (=end of treatment in Example 1) and visit 7 (=end of follow-up in Example 1), respectively, any traceable (routine) CD4 result that had been done since the completion of the initial study (Example 1) as well as the CD4 test which was done as part of the follow up study (Example 2), were evaluated. In order to assess immunological changes since completion of the initial study (Example 1), the last results of the initial study and the last ART naive CD4 result were evaluated. 11 patients (85%) qualified for such an analysis, the two patients that had to be exempted from this analysis had started ART but no CD4 analysis after completion of the phase IIa study (Example 1) and prior to the ART start was done or could be traced.

"Immunological progression" was defined as any CD4 result below 500 cells/mm$^3$ and a drop of 50 cells/mm$^3$ or more from baseline (visit 6 or visit 7, respectively, Example 1) at the follow up examination (Example 2).

Figure 7:
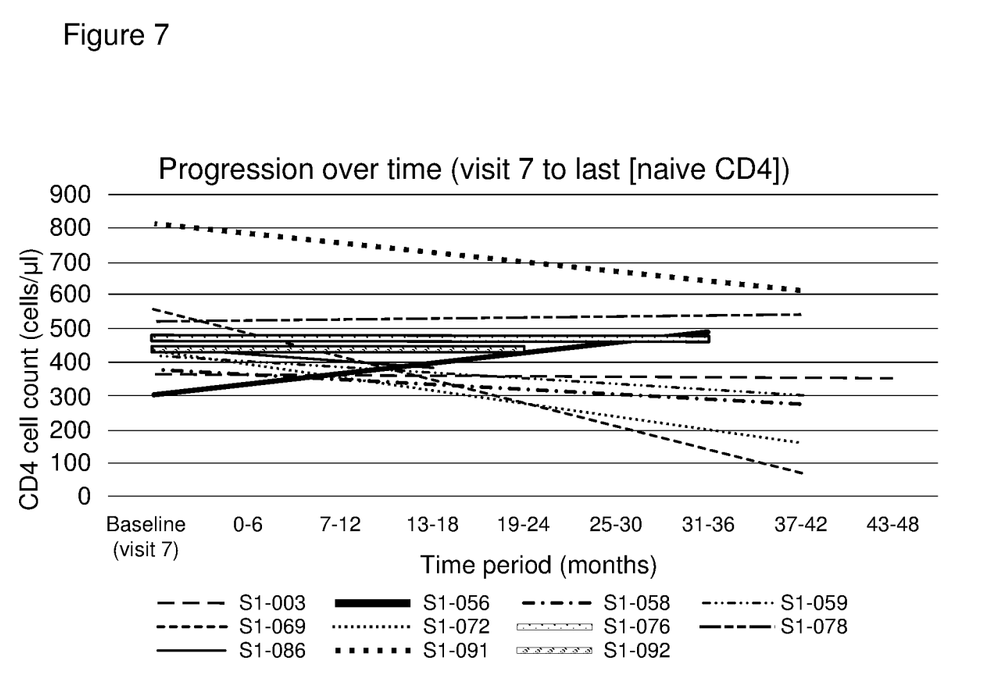
FIG. 7. Immunological progression assessed via $CD4^+$ T cell counts during the period from visit 7 of the phase IIa study and up to 48 months after the visit.

Using visit 6 as reference, five out of 11 patients (45%) did not "progress immunologically" during an observation period of at least 36 months. Taking visit 7 as reference, six out of 11 patients (55%) did not "progress immunologically" during the same observation period (FIG. 7).

Virological status: To assess the virological status, the last viral load results of the initial clinical study (visit 6=end of treatment, visit 7=end of follow-up, Example 1), any traceable (routine) viral load result that has been done since the completion of initial phase IIa study (Example 1) as well as the viral load test which was done as part of the follow up clinical study (Example 2) were evaluated. In order to assess virological changes, since completion of the phase IIa study (Example 1), the last viral load results of the initial study (Example 1) and the last ART naive viral load result were evaluated. six patients (46%) qualified for such an analysis and the seven patients that could not be included into the analysis had all started ART and no viral load tests or results after completion of the initial clinical study (Example 1) or prior to the start of ART treatment were done or could be traced.

Figure 8:
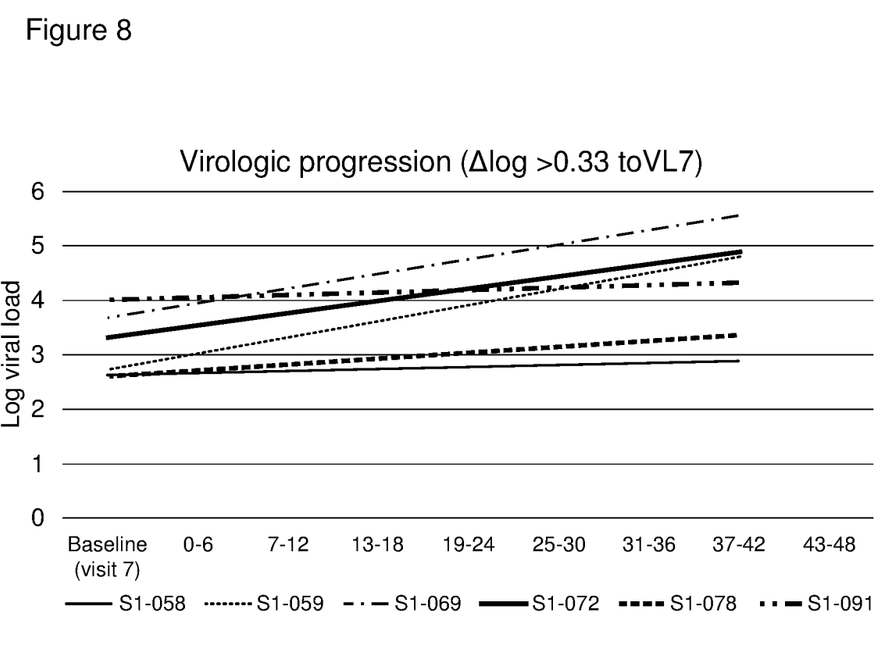
FIG. 8. Virological progression assessed as increase in viral load during the time period from visit 7 of the phase IIa study and up to 48 months after the visit.

"Virological progression" was defined as an increase in viral load of 0.33 log or more from baseline (visit 6 or visit 7, respectively, Example 1) and the last ART naive viral load. Of the six patients that qualified for this analysis, two patients (33%) did not progress virologically, irrespective which visit was chosen as baseline, over a period of at least 37 months (FIG. 8).

Combined immunological and virological progression: Combining the virological results of the six patients for whom virological changes were determined with their immunological results revealed that three (50%) progressed immunologically and virologically, one (17%) did progress immunologically but not virologically, one (17%) did progress virologically but not immunologically, and one (17%) did neither progress virologically nor immunologically. These findings are summarized in Table 3.

TABLE 3

Combined immunological and virological progresssion

|  | Virological Progression | Virological Non-progression |
|---|---|---|
| Immunological Progression | 3 | 1 |
| Immunological Non-progression | 1 | 1 |

CONCLUSION

In conclusion, over a period of 36 to 48 months after four weeks of treatment with a GnRH analogue, about half of the patients who was reevaluated after treatment with the GnRH analogue in the initial clinical study (Example 1) did not progress immunologically and about one third did not progress virologically. Combined, there was one patient (17%) who did neither progress immunologically nor virologically.

Specific embodiments of the invention are given in the list of items:

Item 1

A GnRH analogue for use in minimizing the risk of progression of viral disease.

Item 2. The GnRH analogue for use in minimizing the risk of progression of viral disease according to item 1, wherein the viral disease is selected from Adenovirus Infection, Alphavirus Infection, Arbovirus Encephalitis, Borna Disease, Bunyavirus Infection, Calicivirus Infection, Chickenpox, Condyloma Acuminata, Coronavirus Infection, Coxsackievirus Infection, Cytomegalovirus Infection, Dengue fever, Contageous Ecthyma, Epstein-Barr Virus Infection, Erythema Infectiosum, Hantavirus Infection, Viral Hemorrhagic Fever, Viral Hepatitis, Herpes Simplex, Herpes Zoster, Infectious Mononucleosis, Influenza, Lassa Fever, Measles, Molluscum Contagiosum, Mumps, Paramyxovirus Infection, Phlebotomus Fever, Polyomavirus Infection, Rabies, Respiratory Syncytial Virus Infection, Rift Valley Fever, Rubella, Slow Virus Diseases, Smallpox, Subacute Sclerosing Panencephalitis, Tumor Virus Infections, West Nile Fever, Yellow Fever, and HIV/AIDS.

Item 3. The GnRH analogue for use according to items 1 or 2, wherein the viral disease is HIV/AIDS.

Item 4. The GnRH analogue for use according to any of the preceding items, wherein the GnRH analogue is selected from GnRH I, a GnRH I analogue, GnRH II, a GnRH II analogue, or any pharmaceutically acceptable salts thereof.

Item 5. The GnRH analogue for use according to item 4, wherein the GnRH analogue is a GnRH I analogue.

Item 6. The GnRH analogue for use according to any of the preceding items, wherein the GnRH analogue is a GnRH I analogue selected from deslorelin, avorelin, leuprorelin, triptorelin, buserelin, fertirelin, lutrelin, goserelin, historelin, and nafarelin.

Item 7. The GnRH analogue for use according to any of the preceding items, wherein the GnRH analogue is a GnRH I analogue selected from triptorelin, goserelin, and buserelin.

Item 8. The GnRH analogue for use according to any of the preceding items, wherein the GnRH analogue is buserelin.

Item 9. The GnRH analogue for use according to any one of items 1-4, wherein the GnRH analogue is GnRH II.

Item 10. The GnRH analogue for use according to any one of items 1-4, wherein the GnRH analogue is a GnRH II analogue.

Item 11. A GnRH analogue for use according to any of the preceding items in combination with one or more natural, semi-synthetic or synthetic sex hormones, or any pharmaceutically acceptable salts thereof.

Item 12. A GnRH analogue for use according to item 11, wherein the sex hormone is an androgen or an agent exhibiting a corresponding physiological effect.

Item 13. A GnRH analogue for use according to items 11 or 12, wherein the sex hormone is selected from testosterone, dihydrotestosterone, androsterone, dehydroepiandrosterone, dehydroepiandrosterone, androstenedione, methyltestosterone, and stanozolol.

Item 14. A GnRH analogue for use according to any one of items 11-13, wherein the sex hormone is selected from testosterone, methyltestosterone, and stanozolol.

Item 15. A GnRH analogue for use according to any one of items 11-14, wherein the sex hormone is testosterone.

Item 16. A GnRH analogue for use according to item 11, wherein the sex hormone is an estrogen or an agent exhibiting a corresponding physiological effect.

Item 17. A GnRH analogue for use according to items 11 or 16, wherein the sex hormone is selected from estrogen, estradiol, estriol, estrone, ethynylestradiol, mestranol, dinestrol, diethylstilbestrol, and conjugated estrogens.

Item 18. A GnRH analogue for use according to any one of items 11, 16-17, wherein the sex hormone is selected from estrogen, estradiol, ethynylestradiol, mestranol, dinestrol, and diethylstilbestrol.

Item 19. A GnRH analogue for use according to any one of items 11, 16-18 further in combination with a gestagen or an agent exhibiting a corresponding physiological effect.

Item 20. A GnRH analogue for use according to item 19, wherein the gestagen is selected from progesterone, hydroxyprogesterone, medroxyprogesterone, norethisterone, megestrol, medrogestone, and norgestrel.

Item 21. A pharmaceutical composition comprising a GnRH analogue or any pharmaceutically acceptable salts thereof and a least one pharmaceutically acceptable excipient as defined in any of items 1-20 for use in minimizing the risk of progression of viral disease.

Item 22. A pharmaceutical kit, comprising in a single package:
  i) a first composition comprising a supraphysiological amount of GnRH or a GnRH analogue,
  ii) optionally, a second composition comprising one or more naturally occurring, semi-synthetic or synthetic sex hormones, and
  iii) instructions for use, for use in minimizing the risk of progression of viral disease.

Item 23. The pharmaceutical kit according to item 22, further comprising a third composition comprising a gestagen.

Item 24. The pharmaceutical kit according to items 22 or 23, wherein the viral disease is HIV/AIDS.

Item 25. A method comprising administering to a human or animal subject suffering from a viral disease an effective amount of a GnRH analogue or any pharmaceutically acceptable salts thereof for minimizing the risk of progression of viral disease.

Item 26. A method according to item 25, wherein the effective amount of the GnRH analogue is a supraphysiological amount.

Item 27. The method according to items 25-26, wherein the viral disease is selected from Adenovirus Infection, Alphavirus Infection, Arbovirus Encephalitis, Borna Disease, Bunyavirus Infection, Calicivirus Infection, Chickenpox, Condyloma Acuminata, Coronavirus Infection, Coxsackievirus Infection, Cytomegalovirus Infection, Dengue fever, Contageous Ecthyma, Epstein-Barr Virus Infection, Erythema Infectiosum, Hantavirus Infection, Viral Hemorrhagic Fever, Viral Hepatitis, Herpes Simplex, Herpes Zoster, Infectious Mononucleosis, Influenza, Lassa Fever, Measles, Molluscum Contagiosum, Mumps, Paramyxovirus Infection, Phlebotomus Fever, Polyomavirus Infection, Rabies, Respiratory Syncytial Virus Infection, Rift Valley Fever, Rubella, Slow Virus Diseases, Smallpox, Subacute Sclerosing Panencephalitis, Tumor Virus Infections, West Nile Fever, Yellow Fever, and HIV/AIDS.

Item 28. The method according to items 25-27, wherein the viral disease is HIV/AIDS.

Item 29. The method according to items 25-28, the method further comprising administering to a human or animal subject an effective amount, of one or more natural, semi-synthetic or synthetic sex hormones or pharmaceutically acceptable salts thereof, to compensate for any negative endocrine effects caused by the GnRH analogue.

The invention claimed is:

1. A method to prevent progression of human immunodeficiency virus (HIV) for three years or more in a subject in need thereof, the method comprising:
    administering to said subject a gonadotropin releasing hormone (GnRH) agonist during a treatment period of one to four weeks,
    wherein the GnRH agonist is an adjuvant immunotherapeutic; and
    wherein the administering during the treatment period prevents progression of the HIV in the subject during an immune response maintaining period of three years or more.

2. The method according to claim 1, wherein during the immune response maintaining period, the subject exhibits no symptoms associated with HIV and no progression of the HIV to acquired immunodeficiency syndrome (AIDS).

3. The method according to claim 1, wherein the GnRH agonist is selected from the group consisting of GnRH I, a GnRH I analogue, GnRH II, a GnRH II analogue, and pharmaceutically acceptable salts thereof.

4. The method according to claim 1, wherein the GnRH agonist is selected from the group consisting of deslorelin, avorelin, leuprorelin, triptorelin, buserelin, fertirelin, lutrelin, goserelin, historelin, nafarelin, and pharmaceutically acceptable salts thereof.

5. The method according to claim 1, wherein the GnRH agonist is GnRH II, a GnRH II analogue, or a pharmaceutically acceptable salt thereof.

6. The method according to claim 1, wherein the method further comprises administering one or more naturally-occurring, semi-synthetic, or synthetic sex hormones.

7. The method according to claim 6, wherein the sex hormone is an androgen.

8. The method according to claim 6, wherein the sex hormone is selected from the group consisting of testosterone, dihydrotestosterone, androsterone, dehydroepiandrosterone, dehydroepiandrosterone, androstenedione, methyltestosterone, stanozolol, and pharmaceutically acceptable salts thereof.

9. The method according to claim 6, wherein the sex hormone is an estrogen.

10. The method according to claim 6, wherein the sex hormone is selected from the group consisting of estrogen, estradiol, estriol, estrone, ethynylestradiol, mestranol, dinestrol, diethylstilbestrol, and conjugated estrogens, and pharmaceutically acceptable salts thereof.

11. The method according to claim 6, wherein the method further comprises administering a gestagen.

12. The method according to claim 1, wherein the treatment period is four weeks.

13. The method according to claim 1, wherein the GnRH agonist is administered daily during the treatment period.

14. The method according to claim 4, wherein the GnRH agonist is selected from the group consisting of buserelin, triptorelin, goserelin, and pharmaceutically acceptable salts thereof.

15. The method according to claim 14, wherein the GnRH agonist is buserelin, or a pharmaceutically acceptable salt thereof.

16. The method according to claim 1, wherein the GnRH agonist is not administered to said subject during the immune response maintaining period.

17. The method according to claim 12, wherein the GnRH agonist is not administered to said subject during the immune response maintaining period.

18. The method according to claim 13, wherein the GnRH agonist is not administered to said subject during the immune response maintaining period.

* * * * *